United States Patent [19]

Barnes et al.

[11] 4,284,487
[45] Aug. 18, 1981

[54] OXYGEN ANALYZER PROBE

[75] Inventors: Lyle K. Barnes, Michigan City, Ind.; Richard C. Barringer, Morley, Mich.

[73] Assignee: Milton Roy Company, St. Petersburg, Fla.

[21] Appl. No.: 153,004

[22] Filed: May 27, 1980

Related U.S. Application Data

[63] Continuation of Ser. No. 951,246, Oct. 13, 1978, abandoned.

[51] Int. Cl.³ ............................................. G01N 27/58
[52] U.S. Cl. .................................................. 204/195 S
[58] Field of Search ............................. 204/195 S, 1 S

[56] References Cited

U.S. PATENT DOCUMENTS

| | | | |
|---|---|---|---|
| 3,546,086 | 12/1970 | Sayles | 204/195 S |
| 3,630,874 | 12/1971 | Olette et al. | 204/1 S |
| 3,657,094 | 4/1972 | Hans et al. | 204/195 S |
| 3,758,397 | 9/1973 | Rittiger et al. | 204/195 S |
| 3,784,459 | 1/1974 | Jackson | 204/195 S |
| 3,883,408 | 5/1975 | Kim et al. | 204/195 S |
| 3,928,161 | 12/1975 | McIntyre et al. | 204/195 S |

OTHER PUBLICATIONS

Westinghouse Elec. Corp., Bulletin 106-101, Mar. 1977.

Primary Examiner—G. L. Kaplan
Attorney, Agent, or Firm—Woodcock, Washburn, Kurtz, Mackiewicz & Norris

[57] ABSTRACT

Disclosed is an oxygen analyzer probe for use in situ in the flue gas stream of a furnace of the type having a housing, a solid electrolytic oxygen sensor adjacent to one end of the housing and first and second noble metal leads connected to the sensor. The present invention includes a terminal block within the housing to which the noble metal leads are releasably connected. At the terminal block intermediate leads of a metal dissimilar to the noble metal lead are connected thereto. Since all connections between dissimilar metals are made at the terminal block and since all such connections are at approximately the same temperature, no unbalanced thermocouples are introduced into the electrical path from the sensor. In one embodiment, the intermediate leads are comprised of a nickel alloy and have sufficient rigidity to form the prongs of a male plug connector which prongs extend from the rear end of the housing. A female plug connector mates with the male connector for easy disassembly of the probe during maintenance thereof.

11 Claims, 7 Drawing Figures

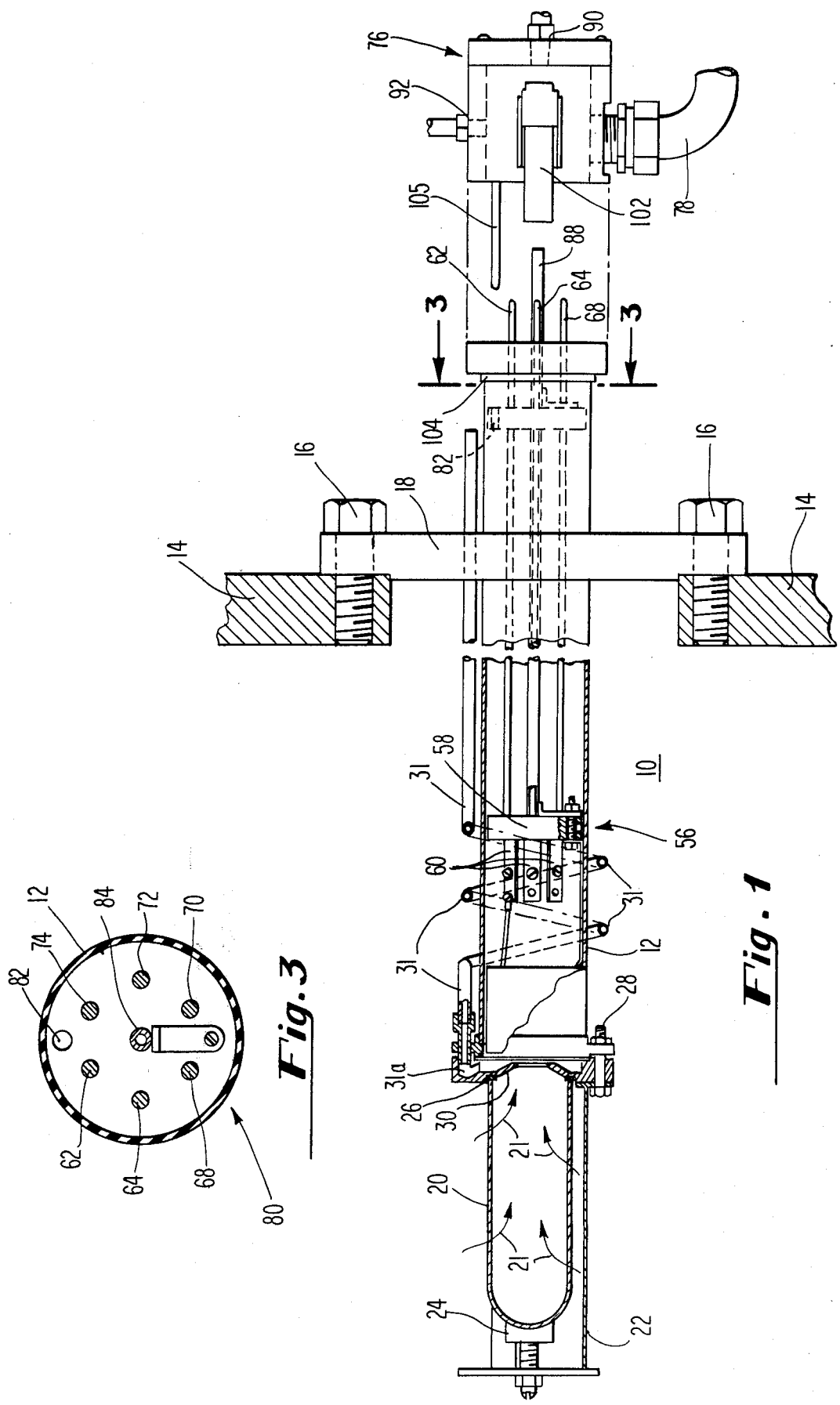

OXYGEN ANALYZER PROBE

This is a continuation of application Ser. No. 951,246, filed Oct. 13, 1978 and now abandoned.

The present invention relates in general to probe type oxygen analyzers and, in particular, it relates to probe type oxygen analyzers positioned in situ in the flue gas of a furnace.

In situ oxygen analyzer probes employing solid electrolytic sensors of for example, zirconium oxide, are used to measure the oxygen content of the flue gases in power plants, blast furnaces, etc. Such probes are subjected to extremely harsh environments and are subject to frequent breakdowns. Because of the harsh environments, noble metal leads, primarily platinum, are generally employed because they are non-reactive in the temperature range to which such probes are subjected, typically up to 1300° f.

The solid electrolytic sensors used in these probes develop an EMF which is proportional to the natural log of the ratio of the partial oxygen pressure of a reference gas to the partial oxygen pressure of the flue gas. This phenomenon is represented by the Nernst equation as follows:

$$EMF = \frac{RT}{4F} \ln \frac{P_1(O_2)}{P_2(O_2)} + C$$

where EMF=sensor output in volts
T=absolute temperature
R=gas constant
F=Farraday constant
$P_1(O_2)$=reference gas partial pressure
$P_2(O_2)$=sample gas partial pressure
C=cell constant Electrical measurement circuitry connected to the probe, in response to this EMF, produces an output related to the partial oxygen pressure of the sample.

In the design of such an oxygen analyzer, it is desirable to minimize the use of platinum or other noble metal leads since these are relatively expensive materials. Accordingly, in at least one prior art probe, namely the Westinghouse model 218 probe, manufactured by Westinghouse Electric Company, the platinum lead emanating from one surface of the sensor is grounded to a stainless steel mounting bracket therefor, which is in turn grounded through intermediate members to the furnace wall. In this manner, the use of platinum is effectively reduced since only one, rather than two, platinum leads are required to pass from the sensor to the electrical measurement circuitry which is also grounded to the furnace wall.

However, one problem associated with the aforementioned Westinghouse probe is that in the ground path from the sensor to the electrical measurement circuitry, numerous junctions between dissimilar metals are found which operate as thermocouples. These thermocouples introduce a source of electrical noise into the measuring circuit by changing the value of C in the aforementioned Nernst equation with temperature. It would be desirable to provide an oxygen analyzer probe having a reduced amount of platinum or other noble metals without introducing unbalanced thermocouples into the electrical path from the probe.

Another disadvantage of the aforementioned prior art probe is that it is difficult to service at the user's site. One reason for this difficulty is that the electrical connections to the probe are hardwired and permanently enclosed in a welded container. It would be desirable to provide an in situ probe which does not have hardwired electrical connections to the sensor to allow for the field maintenance thereof.

These and other objects of the present invention are achieved by means of an oxygen analyzer probe having a housing with a sensor situated at one end thereof and having two noble metal electrical leads extending therefrom. These leads are releasably connected to a terminal block situated within the housing and from there to a plurality of intermediate leads of a metal dissimilar to the noble metal leads. However, unlike the aforementioned prior art probe, since all electrical connections between dissimilar metals are made at the terminal block and thus are all at approximately the same temperature, no unbalanced thermocouples are introduced into the electrical path from the probe. Additionally, in the preferred embodiment, the intermediate leads are comprised of a relatively inexpensive nickel alloy. These intermediate leads project from the other end of the housing and have sufficient rigidity to form the prongs of a male plug type connector. A female plug type connector is adapted to engage the male connector to couple the sensor to an oxygen analyzer circuit. The use of the aforementioned terminal block allows for the servicing of the oxygen analyzer probe at the user's site and the use of the plug type connectors facilitates this onsite servicing.

Another problem associated with prior art probe type oxygen analyzers is the fact that the partial pressure of the oxygen in the sample to be analyzed and the partial pressure of oxygen in the reference gas is dependent upon the total pressure of these gases. Since it is possible for the total gas pressure of the flue gas to vary with respect to the total pressure of the reference gas, errors are introduced into the measurement. It would be desirable to provide a means for insuring that the total pressure of the flue gas being measured and the total pressure of the reference gas employed be an equilibrium. Accordingly, the present invention in one embodiment, employs a probe having an input port for receiving a reference gas and an output port for removing that reference gas from the sensor area. In one embodiment, the output port is directly connected to the flue gas stream which insures that the total pressure of the reference gas and the flue gas are equal. In another embodiment, the output port is connected to a discharge point through an output passageway common to the gas stream. In still another embodiment the output port is connected to the gas stream by means of a pressure regulating means which insures that the pressure of the reference gas and the flue gas are at equilibrium.

The present invention will be more fully understood by reference to accompanying drawings in which:

FIG. 1 is a partial sectional view of an in situ type oxygen analyzer probe incorporating the features of the present invention;

FIG. 3 is a vertical sectional view taken along line 3—3 of FIG. 1; and

Figure 1A:
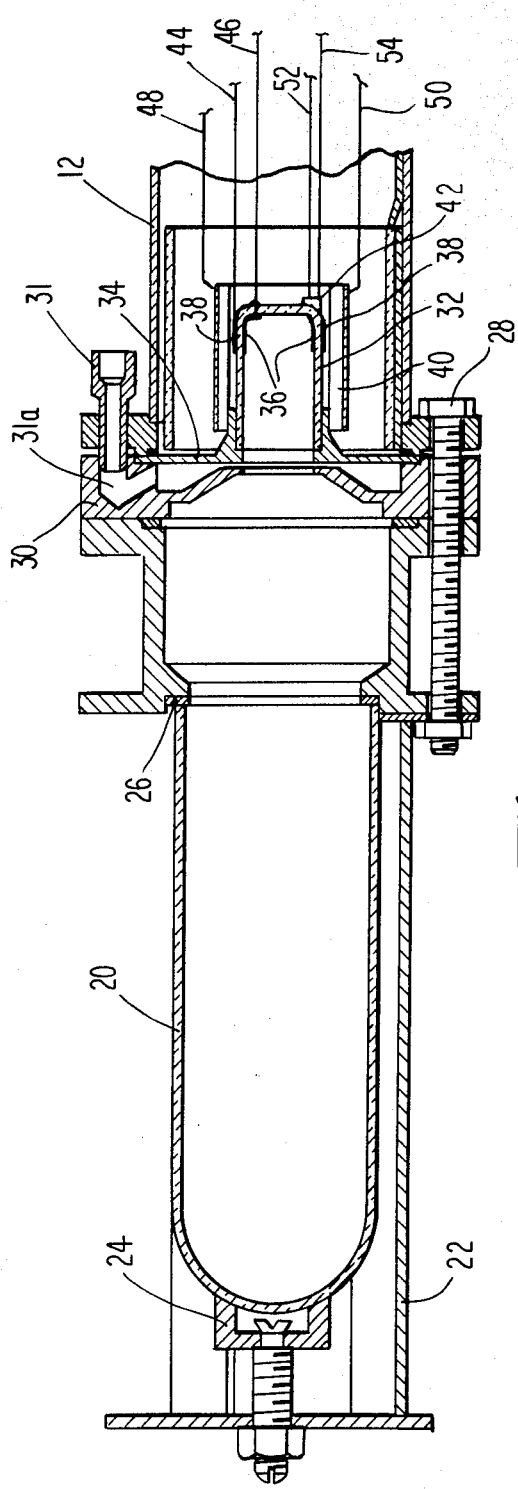
FIG. 1a is an enlarged cross sectional view with a sensor area of FIG. 1.

Referring now to FIG. 1, an in situ type oxygen analyzer probe is shown generally at 10. The probe comprises a housing 12 which is fastened to a furnace wall 14 by means of bolts 16 which pass through a mounting flange 18. Flue gas, inside the furnace wall 14 enters the sensor area at a first end of the housing 12 by diffusion through a ceramic filter 20 as indicated by arrows 21.

As may best be seen in FIG. 1a, the filter 20 is retained and positioned by means of a mounting bracket assembly 22 which comprises a clamp 24 for biasing the filter 20 against the gasket 26 sealing one end of the housing 12. The mounting bracket 22 is retained to the housing 12 by means of bolts, one of which is shown at 28, which also retain a gas distribution cone 30 in a fixed position with respect to the housing 12. Calibration gas conduit 31 connects to a calibration passageway 31a to direct calibration gas of known oxygen pressure to the gas distribution cone 30 and from there to a solid electrolytic oxygen sensor 32 situated within the housing 12. The solid electrolytic oxygen sensor 32 preferably comprises a closed end tube of zirconium oxide. Electrolytic sensor 32 is mounted with ceramic cement to a stainless steel mounting plate 34 which is also clamped to the housing by means of bolts 28.

On one surface of the sensor 32 is a first electrode area 36. Electrode area 36 is comprised of a noble metal, preferably platinum and is formed as an annular band. Situated on the other surface of the sensor 32 is a second electrode 38 which is also preferably formed as an annular band of platinum.

Surrounding and closely abutting the sensor 32 is an annular heating means 40. The heater means 40 preferably comprise an alumina ceramic mandrel with a heater wire wound thereon. Insulation material (not shown) is preferably located between the heater 40 and the housing 12. Also closely abutting the sensor 32 is a temperature sensing element 42 such as a temperature sensitive resistor.

Projecting rearwardly from the first and second electrodes 36 and 38 are first and second electrical leads 44 and 46 respectively which are also comprised of a noble metal, preferably platinum. The second lead 46 preferably passes through an opening in the sensor 32 which is gas sealed as it is directed rearwardly from the first electrode 36.

Also passing rearwardly are third and fourth electrical leads 48 and 50 which are connected to the heater 40. Finally, also passing rearwardly are fifth and sixth electrical leads 52 and 54 which are connected to the temperature sensing element 42.

It is extremely important that the temperature of the aforementioned sensor 32 remain constant as the temperature inside the furnace wall 14 changes. Accordingly, the temperature sensing element 42 monitors the temperature of the sensor 32 and controls (through circuitry not shown) the current flowing through heater 40.

In the prior art Westinghouse device referred to above, only one electrical lead to the electrolytic sensor therein (similar to either lead 44 or 46 herein) passes rearwardly. In place of the other of these leads, the electrode area which would be connected thereto, is connected directly to an intermediate metal mounting piece such as mounting plate 34 and from there to the housing. The housing is then connected to the grounded furnace wall. This arrangement leads to the unbalanced thermocouples referred to above since the junction between the mounting plate and housing and the function between the housing and the furnace wall are junctions between dissimilar metals.

Additionally, the electrical lead to the sensor in the aforementioned Westinghouse probe which does pass rearwardly, does so along the entire length of the housing, using substantial amounts of platinum since probes are manufactured in standard 1.5, 3, 6, 9 and 12 foot lengths.

In accordance with the present invention, instead of passing rearwardly along the entire length of the housing 12 the first and second platinum leads 44 and 46 are directed rearwardly only as far as a terminal block shown generally at 56. The terminal block 56 is situated proximate to the first end of the housing 12 and is therefore situated in the hot zone of the furnace with which the probe of the present invention is utilized. Preferably, also directed to the terminal block are third and fourth leads 48 and 50 emanating from the heater 40 and the fifth and sixth electrical leads 42 and 54 emanating from the temperature sensing element 42. The terminal block 56 preferably comprises a ceramic bushing 58. Mounted upon the bushing 58 are a plurality of terminals 60 to which the electrical leads 44 through 54 are releasably connected. Passing through the bushing 58 and in electrical communication with the terminal 60 are a plurality of intermediate electrical leads 62, 64, 68, 70, 72 and 74. These intermediate leads are formed of a material dissimilar to the noble metal leads 44, 46, 52 and 54. Since all of the connections between noble metal leads 44 through 54 and the dissimilar metal intermediate leads 62 through 74 are made at terminal block 56, all connections are made at approximately the same temperature zone within the furnace thus eliminating the likelihood of unbalanced thermocouples.

In accordance with one aspect of the present invention, the intermediate electrical leads 62 through 74 are formed of a nickel alloy which is stable at high temperatures i.e. temperatures up to 1300° f. This nickel alloy preferably comprises a nickel chromium iron alloy such as nichrome or Inconel. By Inconel is meant a nickel chromium iron alloy consisting essentially of 79% nickel, 13.5% chromium and 7% iron by weight.

Due to the fact that the aforementioned nickel alloys are poor conductors, relatively large diameter intermediate leads 62 through 74 must be employed. In the preferred embodiment of the present invention, the intermediate leads 62 through 74 pass rearwardly through the housing 12 and project from a second or rear end thereof and the diameters of the intermediate leads are chosen not only to carry sufficient current and keep resistance low but also to have sufficient rigidity to form the prongs of a male plug type connector. A releasable electrical connector such as a female plug type connector shown generally at 76 is adapted to mate with the ends of the intermediate lead 62 through 74. A lead bundle 78 emanating from the female plug connector 76 is directed to the electrical measuring circuitry of an oxygen analyzer wherein the output of the sensor 32 may be analyzed.

As may best be seen from FIG. 3, it is desirable to provide an insulating spacer 80 for retaining the intermediate lead 62 through 74 in the proper orientation as they project from the housing 12. This insulating spacer 80 is preferably comprised of Teflon for reasons which will be more fully explained below and it contains apertures therein for receipt of each of the intermediate leads as well as two additional apertures 82 and 84, the function of which will also be described below. Passing through the aperture 84 and extending along the central axis of the length of the housing 12 is a reference gas conduit 88 which also passes through the ceramic bushing 58 of the terminal block 56. Reference gas passing through the reference gas conduit 88 projects upon the surface of the sensor 32 which is in the interior of the housing 12. The reference gas conduit, like the intermediate leads 62 through 74 also projects from the end of the housing 12 and engages the female plug connector 76.

The female plug connector 76 preferably includes a threaded reference gas inlet port 90 which communicates with the reference gas conduit 88. The female plug connector 76 also includes a threaded reference gas outlet port 92 which communicates with the interior of the housing 12 such that reference gas may be removed therefrom after measurements have been obtained.

Figure 2:
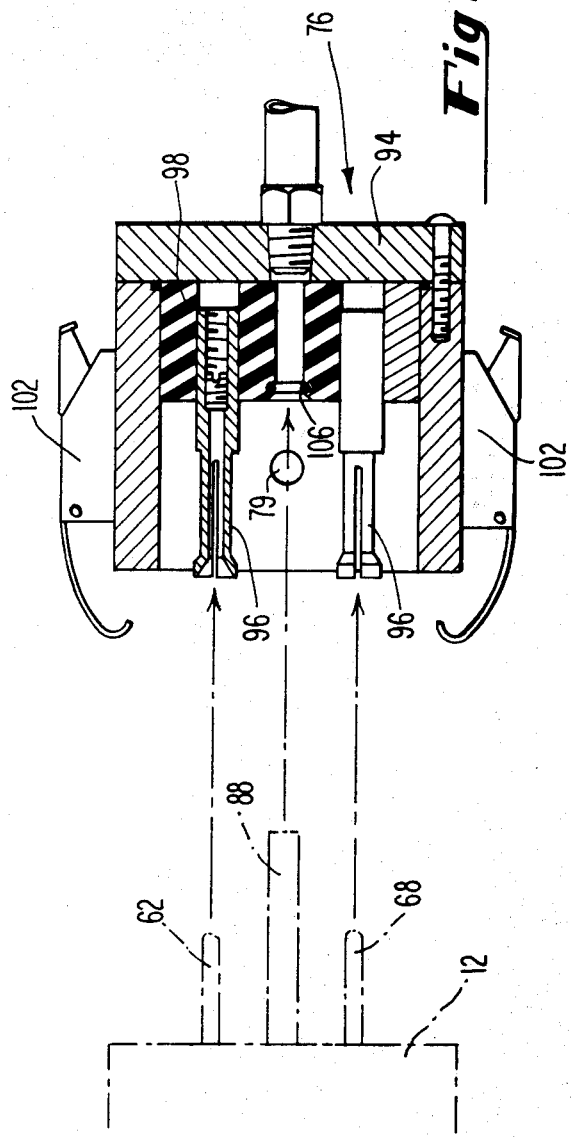
FIG. 2 is a horizontal sectional view through the female type plug connector shown in FIG. 1.

Referring now to FIG. 2, the female plug connector 76 will be more fully described. That connector includes a body portion 94 having a plurality of metallic sleeves 96 open towards the projecting ends of the intermediate leads 62 through 74 for their insertion. The length of the sleeves 96 is substantially longer than the length of the projecting portion of the intermediate leads to provide for the differential expansion of those leads as the temperature of the furnace in which the probe 10 is situated varies. To compensate for this expansion, the insulating spacer 80 described above is formed of Teflon to allow for the sliding of the spacer along the interior surface of the housing 12 as the leads 62 through 74 expand or contract. The metallic sleeves 96 are imbedded in insulating block 98. Electrical connectors leading from the lead bundle 78 enter through aperture 79 and place electrical measurement circuitry in electrical communication with the sleeves 96. The female plug connector 76 is retained to the housing by means of releasable snap connectors 102 which mate with a flange 104 formed at the rearward end of the housing 12. Additionally, the female plug connector 76 may contain a locating prong 105 which mates with the aforementioned aperture 82 in the insulating spacer 80 to insure that the intermediate leads 62 through 74 engage the proper one of the sleeves 96. Finally, the female plug connector 76 contains a flexible "o" ring 106 therein which mates with the projecting end of the reference gas conduit 88 to insure an adequate seal therewith.

In servicing the probe 10 of the present invention at a user's site, the female plug connector 76 is removed from the male plug connector thus removing the probe from electrical measurement circuitry. The probe may then be removed from the furnace by removing bolts 16. Next, by releasing bolts 28, the sensor 32, heater 40 and temperature sensing element 42 may be slid forward from the housing 12 along with the intermediate lead 62 through 74 thereby exposing the terminal block 56. The leads 44 through 54 may then be released from the terminals 60 to allow for replacement of the probe 32, heater 40 or temperature sensor 44 if required.

Figure 4A:
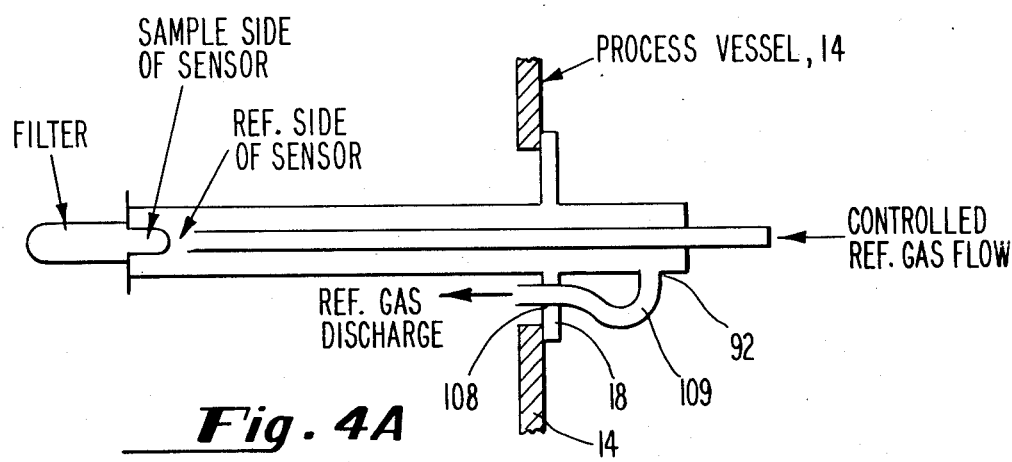
FIGS. 4a–4c are schematic views of three separate embodiments for insuring that the total pressure of flue gas and reference gas used in accordance with the present invention are in equilibrium.
Figure 4B:
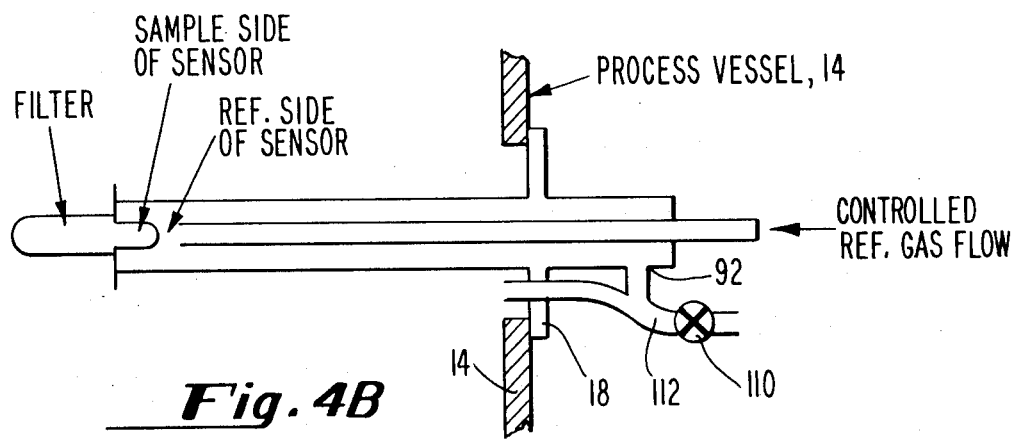

Referring now to FIG. 4a, a means disclosed for insuring that the reference gas flowing through reference gas conduit 88 is at the same total pressure as the flue gas inside the process vessel or furnace wall 14. In the embodiment shown in FIG. 4a, the reference gas outlet 92 is directly connected to the interior side of furnace wall 14 through an aperture 108 in flange 18 by a length of tubing 109.

Figure 4C:
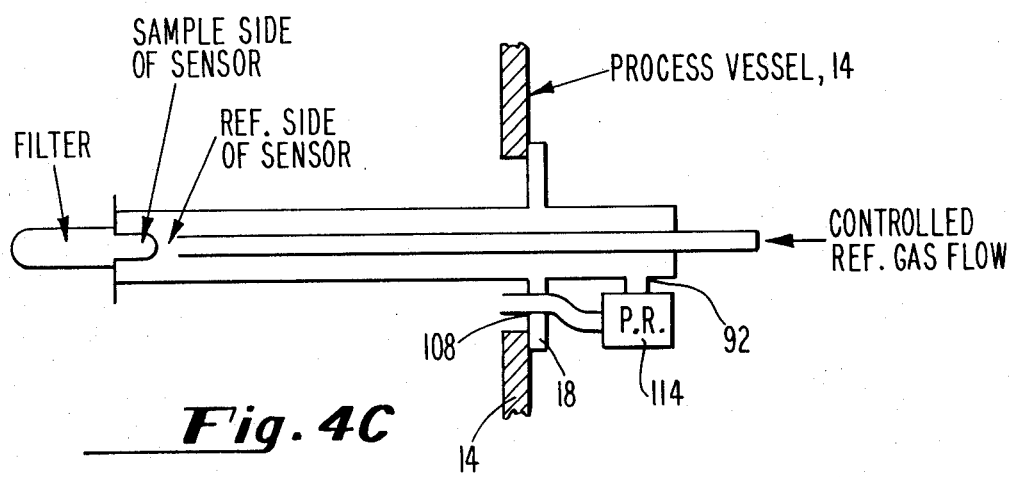

While the arrangement shown in FIG. 4a is adequate for many purposes, in certain applications it is undesirable to direct reference gas into the process gas stream inside the furnace wall 14 since to do so may effect the oxygen pressure being measured. Therefore, in accordance with a preferred aspect of the present invention, instead of directly connecting the output port 92 to aperture 108, output 92 port may be connected to a discharge point through a valve 110 by means of an output passageway 112 which is common to the interior of housing 12 and to the gas stream inside the furnace walls 14. This discharge point may be for example at atmospheric pressure. In an alternative embodiment shown in FIG. 4c, the output port 92 may be connected to the aperture 108 in flange 18 by a pressure regulating means 114.

While particular embodiments of the present invention have been shown and described, various modifications are within the true spirit and scope of the invention. The appended claims are, therefore, intended to cover all such modifications.

What is claimed is:

1. An oxygen analyzer probe for use in situ in a flue gas stream of a furnace of the type having a housing with a first end adapted to be situated in said furnace and a second end adapted to be external thereto, a solid electrolytic oxygen sensor adjacent said first end of said housing, a first electrode on one side of said sensor, a second electrode on the other side of said sensor, a first noble metal lead connected to said first electrode and a second noble metal lead connected to said second electrode, the improvement comprising:

a terminal block within said housing, said terminal block being more proximate to said first than to said second end, said first and said second noble metal leads being releasably connected to said terminal block;

first and second intermediate leads connected to said first and said second noble metal leads respectively at said terminal block, said first and said second intermediate leads being comprised of a metal dissimilar to said first and said second noble metal leads, and an electrical connector external to said housing, said intermediate leads being electrically connected to an oxygen analyzer circuit at said connector.

2. The oxygen analyzer probe of claim 1 wherein said intermediate leads project from said second end of said housing, said intermediate leads having sufficient rigidity to form the prongs of a male plug type connector; said electrical connector comprising a female plug type connector adapted to engage said male connector prongs whereby said connection to said oxygen analyzer circuit is achieved.

3. The oxygen analyzer probe of claim 2 further comprising:

a heater means adjacent said sensor;
third and fourth electrical leads connected to said heater means;
third and fourth intermediate leads, one end of each being releasably connected to said third and said fourth electrical leads respectively at said terminal block, the other end of said third and said fourth intermediate leads projecting from said second end of said housing and having sufficient rigidity to form prongs of said male plug type connector.

4. The oxygen analyzer probe of claim 3 further comprising:

a temperature sensor adjacent said sensor;

fifth and sixth electrical leads connected to said temperature sensor;

fifth and sixth intermediate leads, one end of each being releasably connected to said fifth and sixth electrical leads respectively at said terminal block, the other end of said fifth and said sixth intermediate leads projecting from said second end of said housing and having sufficient rigidity to form prongs of said male plug type connector.

5. The oxygen analyzer probe of claim 4 wherein said third, fourth, fifth and sixth intermediate leads comprise a nickel alloy.

6. The oxygen analyzer probe of claim 1 wherein said dissimilar metal comprises a nickel alloy.

7. The oxygen analyzer probe of claim 6 wherein nickel alloy comprises a nickel chromium alloy.

8. The oxygen analyzer probe of claim 7 wherein said nickel chromium alloy comprises a nickel chromium iron alloy.

9. The oxygen analyzer probe of claim 8 wherein said nickel chromium iron alloy comprises nichrome.

10. The oxygen analyzer probe of claim 8 wherein nickel chromium iron alloy consists essentially of 79% nickel, 13.5% chromium and 7% iron by weight.

11. The oxygen analyzer probe of claim 1 further comprising a gas distribution cone for directing said flue gas and calibration gases toward the surface of said sensor.

* * * * *